United States Patent [19]

Kirmann

[11] Patent Number: Plant 6,072

[45] Date of Patent: Dec. 29, 1987

[54] GERANIUM PLANT NAMED LUCY

[75] Inventor: Wolfgang Kirmann, Langenzersdorf, Austria

[73] Assignee: Mirko Vavra, Bisamberg, Austria

[21] Appl. No.: 810,672

[22] Filed: Dec. 19, 1985

[51] Int. Cl.[4] ..... A01H 5/00
[52] U.S. Cl. ..... Plt./68
[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A geranium plant named Lucy having pale lavender-pink flower color, variegated with dark red-purple on upper petals and lower petals having a white center; vigorous, compact growth habit; early flowering; good bud production at night temperatures up to 16° C., thus providing a long and continuous flowering period; and ease of propagation and good rooting habit.

2 Drawing Figures

The present invention comprises a new and distinct cultivar of geranium, botanically known as *Pelargonium domesticum,* and hereinafter referred to by the cultivar name Lucy.

Lucy is a product of a planned breeding program which had the objective of creating new geranium cultivars having an early flowering response and long flowering period, good flower production, compact growth habit, and pale lavender flower color variegated with deeper red-purple.

Lucy was originated from a hybridization made by applicant in a controlled breeding program in Bisamberg, Austria in 1980. The female parent was Venedig, a cultivar characterized by its compact growth habit, excellent flower production and lilac flower color. The male parent of Lucy was a cultivar designated as seedling 008/79 having a compact, broad growth habit, relatively large foliage and white flower color with lilac markings.

Lucy was discovered and selected as one flowering plant within the progeny of the stated cross by applicant on Mar. 3, 1981 in a controlled environment in Bisamberg, Austria.

The first act of asexual reproduction of Lucy was accomplished when vegetative cuttings were taken from the initial selection on Aug. 30, 1981 in a controlled environment in Bisamberg, Austria by a technician working under formulations established and supervised by Wolfgang Kirmann. Horticultural examination of selected units initiated in the spring of 1982 has demonstrated that the combination of characteristics as herein disclosed for Lucy are firmly fixed and are retained through successive generations of asexual reproduction.

Lucy has not been observed under all possible environmental conditions. The phenotype may vary significantly with variations in environment such as temperature, light intensity, and day length. The following observations, measurements and comparisons describe plants grown in Bisamberg, Austria under conditions which approximate those generally used in commercial practice.

The following traits have been repeatedly observed and are determined to be basic characteristics of Lucy, which in combination distinguish this geranium as a new and distinct cultivar.

1. Pale lavender-pink flower color with white at the base of the lower petals, and variegated with darker red-purple on the upper petals.
2. Good bud production and very floriferous.
3. Medium green foliage.
4. Vigorous, compact growth habit.
5. Early flowering and long flowering period.
6. Buds are produced under normal greenhouse conditions (5000 Lux for 16 hours per day) at 14°-16° C. This is well above the cooler temperatures required for previous *domesticum* varieties. In addition, plants flowered indoors can be transplanted outdoors and will continue blooming at night temperatures as high as 16° C. Known *domesticum* cultivars will produce buds outdoors only at night temperatures of 10° C. or lower.
7. Lucy is unique with regard to the combined features of compactness, continuous flowering, floriferous habit, and pale lavender-pink flower color.

Of the many commercial cultivars known to the present inventor, the most similar in comparison to Lucy is Jubilante, an unpatented but commercial cultivar. In comparison to Jubilante, Lucy has a more compact growth habit, flowers much earlier, has a different flower color, and is more floriferous.

The accompanying photographic drawings show typical flower and foliage characteristics of Lucy, with colors being as true as possible with illustrations of this type.

Sheet 1 is a perspective view of a potted plant of Lucy.

Sheet 2 is a black and white print showing the upper surface of immature and mature plants of Lucy.

In the following description color references are made to The Royal Horticultural Society Color Chart (RHS). The color values were determined at 9:00 a.m. on May 23, 1985 under 35,000 Lux light intensity in a greenhouse at Hillscheid, Federal Republic of Germany.

Classification:

*Botanical.*—*Pelargonium domesticum.*

*Commercial.*—Commonly referred to as a "Martha Washington" geranium, and having the cultivar name Lucy.

INFLORESCENCE

A. Umbel:

*Average diameter.*—Medium, 95–120 mm.
*Peduncle length.*—Normal.
*Pedicel length.*—Normal.

B. Corolla:
*Average diameter.*—65–80 mm; total inflorescence diameter is within the foliage.
*Form.*—Five-six petals.
*Color (general tonality from a distance of three meters).*—Pale lavender-pink with white at base of lower petals; upper petals variegated with darker red-purple.
*Color (upper surface).*—68D, with white on lower petals; upper petals variegated with 70B, and darker 60B in center of variegation.

C. Bud:
*Shape.*—Elongated.
*Color.*—White with lilac.

D. Reproductive organs:
*Androecium.*—Reddish-yellow, 7–8 stamens.
*Gynoecium.*—Five to seven lobed stigma.

E. Spring flowering response period: Early.

G. Durability: Good.

PLANT

A. Foliage:
*Form.*—Zygomorphic with a nectar spur.
*Margin.*—Crenate to serrate and indented.
*Color (upper surface).*—Medium green.
*Tolerance of botrytis and soil fungi.*—Good.

B. General appearance and form:
*Internode length.*—Short.
*Branching pattern.*—Good.
*Height.*—Very compact.

I claim:

1. A new and distinct cultivar of geranium named Lucy, as described and illustrated, and particularly characterized by its pale lavender-pink flower color, variegated with dark red-purple on upper petals and lower petals having a white center; vigorous, compact growth habit; early flowering; good bud production at night temperatures up to 16° C.; thus providing a long and continuous flowering period; and ease of propagation and good rooting habit.

* * * * *

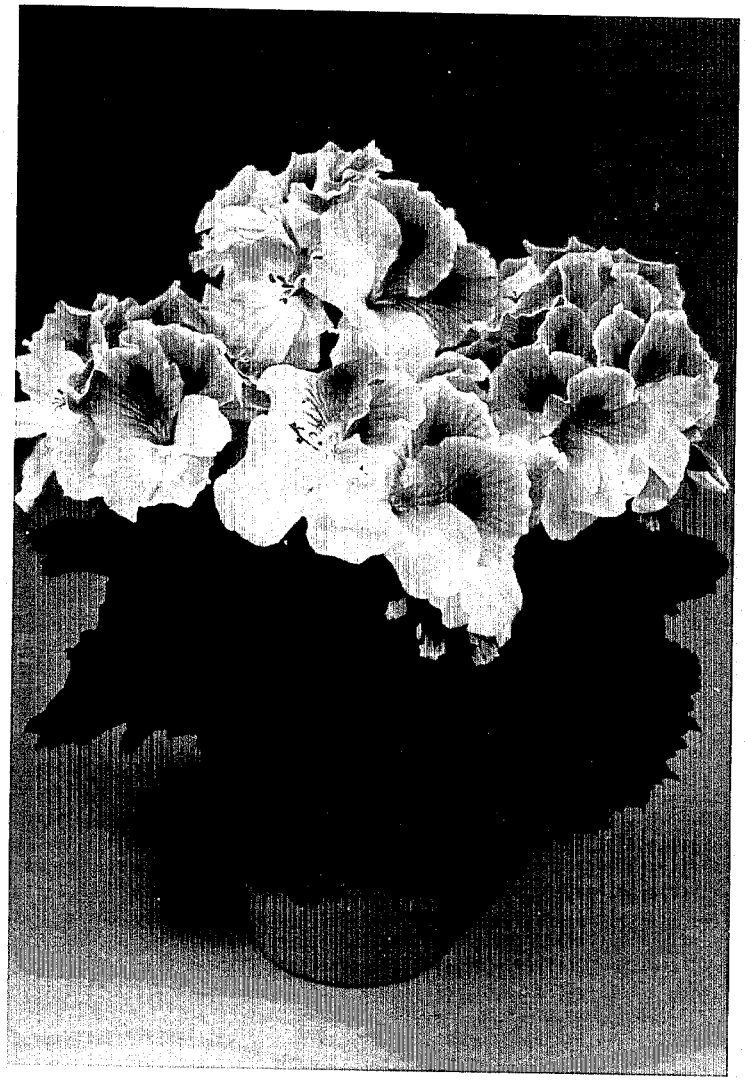

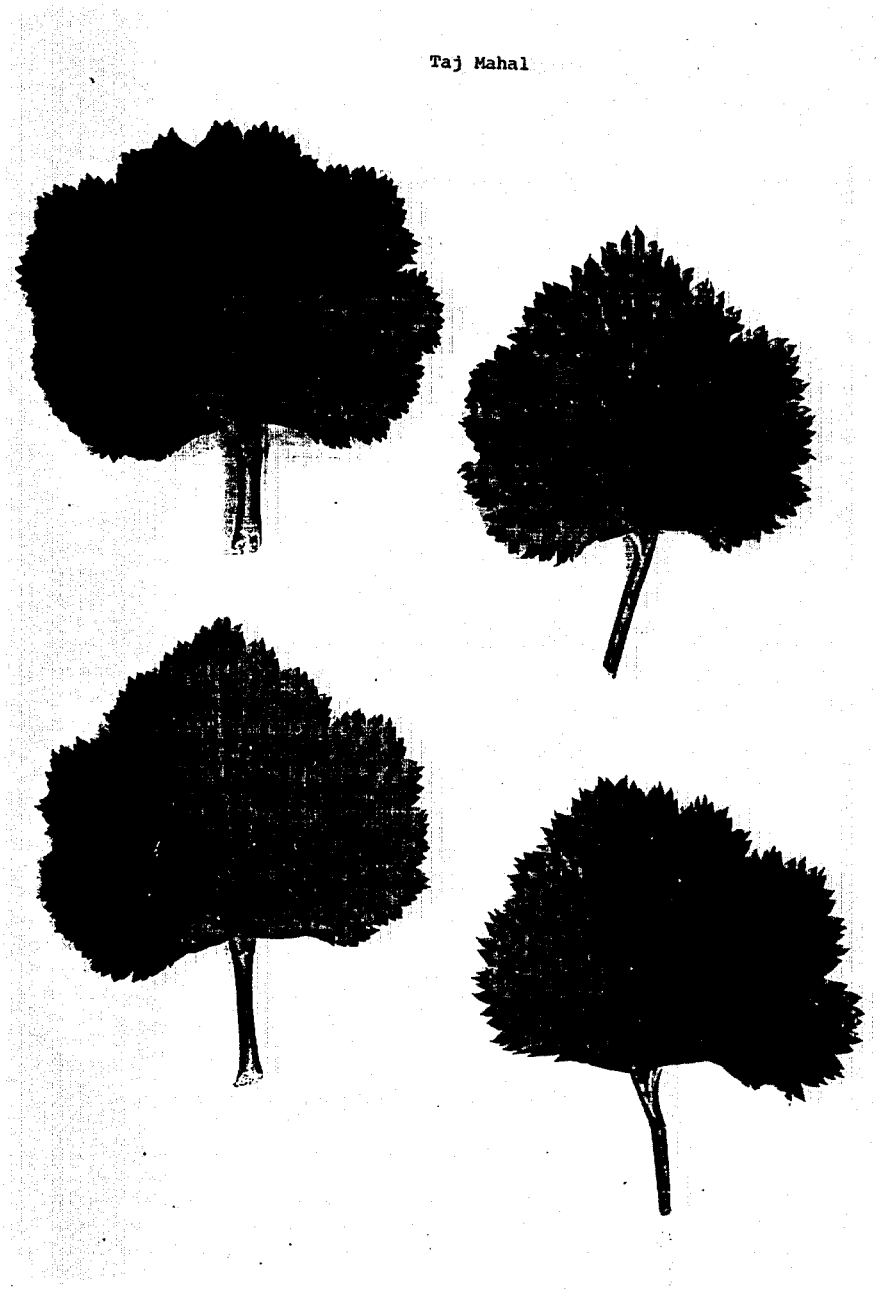

Taj Mahal